US011723801B2

(12) United States Patent
Dam-Huisman

(10) Patent No.: US 11,723,801 B2
(45) Date of Patent: Aug. 15, 2023

(54) METHOD AND SYSTEM FOR ACTIVE IRRIGATION OF AN OPHTHALMIC SURGICAL SITE

(71) Applicant: Crea IP B.V., Vierpolders (NL)

(72) Inventor: Adriaantje Coliene Dam-Huisman, Delfgauw (NL)

(73) Assignee: Crea IP B.V., Vierpolders (NL)

( * ) Notice: Subject to any disclaimer, the term of this patent is extended or adjusted under 35 U.S.C. 154(b) by 396 days.

(21) Appl. No.: 16/762,386

(22) PCT Filed: Oct. 23, 2018

(86) PCT No.: PCT/NL2018/050701
§ 371 (c)(1),
(2) Date: May 7, 2020

(87) PCT Pub. No.: WO2019/093882
PCT Pub. Date: May 16, 2019

(65) Prior Publication Data
US 2020/0360594 A1    Nov. 19, 2020

(30) Foreign Application Priority Data
Nov. 10, 2017 (NL) .................................... 2019887

(51) Int. Cl.
*A61F 9/007* (2006.01)
*A61M 1/00* (2006.01)
*A61M 3/02* (2006.01)

(52) U.S. Cl.
CPC .......... *A61F 9/00736* (2013.01); *A61F 9/007* (2013.01); *A61M 1/743* (2021.05);
(Continued)

(58) Field of Classification Search
CPC .. A61F 9/007; A61F 9/00736; A61F 9/00781; A61M 2205/3331;
(Continued)

(56) References Cited

U.S. PATENT DOCUMENTS 3,927,671 A * 12/1975 Chittenden ......... A61M 3/0241
604/80
4,909,786 A * 3/1990 Gijselhart ........... A61M 5/1689
128/DIG. 13
(Continued)

FOREIGN PATENT DOCUMENTS

CA    2800850 A1 * 12/2011 ......... A61F 9/00736
CN    104640523 B * 7/2017 ......... A61F 9/00745
(Continued)

*Primary Examiner* — Scott J Medway
(74) *Attorney, Agent, or Firm* — N.V. Nederlandsch Octrooibureau

(57) ABSTRACT

An active irrigation system for controlling delivery of irrigation fluid to a surgical site includes a chamber having at least one fluid port for introducing an irrigation fluid from a fluid source into the chamber and delivering the irrigation fluid to a surgical site. A variable pressure source is provided in fluid communication with the chamber and is configured to pressurize the chamber. A pressure sensor also in fluid communication with the chamber monitors the pressure within the chamber and a controller adjusts the variable pressure source to maintain the desired irrigation pressure within the chamber.

10 Claims, 6 Drawing Sheets

(52) U.S. Cl.
CPC ............ *A61M 1/77* (2021.05); *A61M 3/0201* (2021.05); *A61M 3/0245* (2013.01); *A61M 3/0258* (2013.01); *A61B 2217/005* (2013.01); *A61B 2217/007* (2013.01); *A61M 2205/18* (2013.01); *A61M 2205/3331* (2013.01); *A61M 2205/3389* (2013.01); *A61M 2210/0612* (2013.01)

(58) Field of Classification Search
CPC .. A61M 2205/3389; A61M 2210/0612; A61M 3/0216; A61M 3/0233; A61M 1/74; A61M 1/0058; A61M 2205/3337; A61M 3/0237; A61M 1/77
See application file for complete search history.

(56) References Cited

U.S. PATENT DOCUMENTS

| | | | | | |
|---|---|---|---|---|---|
| 4,935,005 | A | * | 6/1990 | Haines | A61M 1/742 604/35 |
| 5,242,434 | A | * | 9/1993 | Terry | A61M 1/882 604/326 |
| 5,865,764 | A | * | 2/1999 | Moorhead | A61M 3/0258 600/561 |
| 5,885,240 | A | * | 3/1999 | Bradbury | A61M 1/0023 604/4.01 |
| 6,030,359 | A | * | 2/2000 | Nowosielski | A61M 3/0216 604/67 |
| 6,491,661 | B1 | * | 12/2002 | Boukhny | A61M 1/0058 606/107 |
| 6,579,255 | B2 | * | 6/2003 | Kadziauskas | A61F 9/00745 604/35 |
| 8,465,467 | B2 | * | 6/2013 | Gao | A61M 1/74 604/118 |
| 8,469,050 | B2 | * | 6/2013 | King | A61M 31/00 137/392 |
| 8,652,089 | B2 | * | 2/2014 | Kumar | A61M 1/777 600/101 |
| 10,488,848 | B2 | * | 11/2019 | Peret | G05B 19/416 |
| 11,110,218 | B2 | * | 9/2021 | Kuntz | A61M 1/74 |
| 2002/0019607 | A1 | * | 2/2002 | Bui | A61M 1/0058 604/67 |
| 2005/0228423 | A1 | * | 10/2005 | Khashayar | A61F 9/00745 606/107 |
| 2006/0052666 | A1 | * | 3/2006 | Kumar | A61M 3/0258 600/159 |
| 2007/0083150 | A1 | | 4/2007 | Nazarifar et al. | |
| 2008/0125697 | A1 | | 5/2008 | Gao | |
| 2009/0099498 | A1 | | 4/2009 | Demers et al. | |
| 2017/0273826 | A1 | | 9/2017 | Sanchez, Jr. | |

FOREIGN PATENT DOCUMENTS

| | | | | |
|---|---|---|---|---|
| EP | 3007660 B1 | * | 5/2017 | ............ A61F 9/007 |
| EP | 3318291 A1 | * | 5/2018 | .......... A61M 1/0058 |
| JP | 2002153499 A | | 5/2002 | |
| JP | 2008500879 A | | 1/2008 | |
| JP | 2009509632 A | | 3/2009 | |
| JP | 2011000202 A | | 1/2011 | |
| WO | 2017163202 A1 | | 9/2017 | |

* cited by examiner

METHOD AND SYSTEM FOR ACTIVE IRRIGATION OF AN OPHTHALMIC SURGICAL SITE

FIELD OF THE INVENTION

The present invention relates to an apparatus for irrigation of an ophthalmic surgical site and methods for controlling such apparatus. In particular, the present invention relates to a system for active irrigation in which the irrigation pressure can be precisely controlled.

BACKGROUND ART

During ophthalmic surgery, fluid is typically infused into the eye and aspirated therefrom. To prevent damage to the eye tissue or collapse of the surgical site, aspiration and irrigation systems aim to maintain a stable pressure within the eye.

US patent publication US2008/125697 describes an ophthalmic surgical system comprising an irrigation line through which an irrigation fluid is delivered to the surgical site. The system also comprises an aspiration line, through which aspirated fluid and tissue can be evacuated from the surgical site. The flow of irrigation fluid from the infusion bottle/bag is controlled by the vacuum produced at the surgical site by the aspiration apparatus and/or pressurization of an irrigation fluid source, e.g. by squeezing a bag or bottle containing irrigation fluid.

US patent publication US2007/083150 discloses a method for intraocular pressure control using measured flow rate in a fluid line and a dual infusion chamber, with the intent to prevent too high a pressure in a patient's eye. From the measured flow rate, a predicted intraocular pressure is calculated, and depending on an operator input of desired pressure, infusion is adjusted. A dual infusion chamber is provided to allow continued fluid flow if one of the infusion chambers is (almost0 empty.

SUMMARY OF THE INVENTION

The present invention seeks to provide an improved surgical irrigation system, which provides for active irrigation of the surgical site by controlling the irrigation pressure.

According to a first aspect of the invention, there is provided an active irrigation system for controlling delivery of irrigation fluid to a surgical site, the irrigation system comprising: a chamber having at least one fluid port for introducing an irrigation fluid from a fluid source into the chamber and delivering the irrigation fluid to a surgical site; an irrigation pump configured to deliver irrigation fluid from the fluid source to the chamber; a variable pressure source in fluid communication with the chamber and configured to pressurize the chamber; a pressure sensor in fluid communication with the chamber configured to monitor the pressure in the chamber; a controller configured to adjust the pressure applied by the variable pressure source to maintain the desired irrigation pressure within the chamber.

According to a second aspect of the invention, there is provided a method for actively controlling irrigation pressure within a surgical irrigation system, the method comprising: moving an irrigation fluid from a fluid source through a fluid port into a chamber using an irrigation pump; pressurizing the chamber using a variable pressure source in fluid communication with the chamber via a pressure port by applying a predetermined pressure to move the fluid from the chamber, through the fluid port (or a dedicated outlet port); measuring the pressure within the chamber with a pressure sensor in fluid communication with the chamber; and adjusting the pressure applied by the variable pressure source in response to feedback from the pressure sensor to maintain a predetermined irrigation pressure within the chamber.

By actively controlling the irrigation pressure in the chamber with a variable pressure source, precise control of the pressure within the eye is possible, which may be even further improved by taking into account further (pneumatic) system parameters, such as tube and needle diameters. This reduces the risk of damage to delicate ocular tissue due to excessive pressure in the eye and minimizes the chance of the eye collapsing due to a lack of fluid at the surgical site.

Further embodiments are described in the claims as attached.

SHORT DESCRIPTION OF DRAWINGS

The present invention will be discussed in more detail below, with reference to the attached drawings, in which.

DESCRIPTION OF EMBODIMENTS

Exemplary embodiments of the present invention will now be described in detail. The skilled person will understand that devices and methods described herein are non-limiting exemplary embodiments and that the scope of protection is defined by the claims. For example, although the present invention is described with respect to ophthalmic aspiration and/irrigation procedures, the skilled person will understand that the present invention may be used in other applications, for example in other aspiration and/or irrigation systems, e.g. fine needle aspiration procedures. The skilled person will also understand that the features illustrated or described in connection with one exemplary embodiment may be combined with features described in other exemplary embodiments. Such modifications and variations are included within the scope of the present disclosure.

Figure 1:
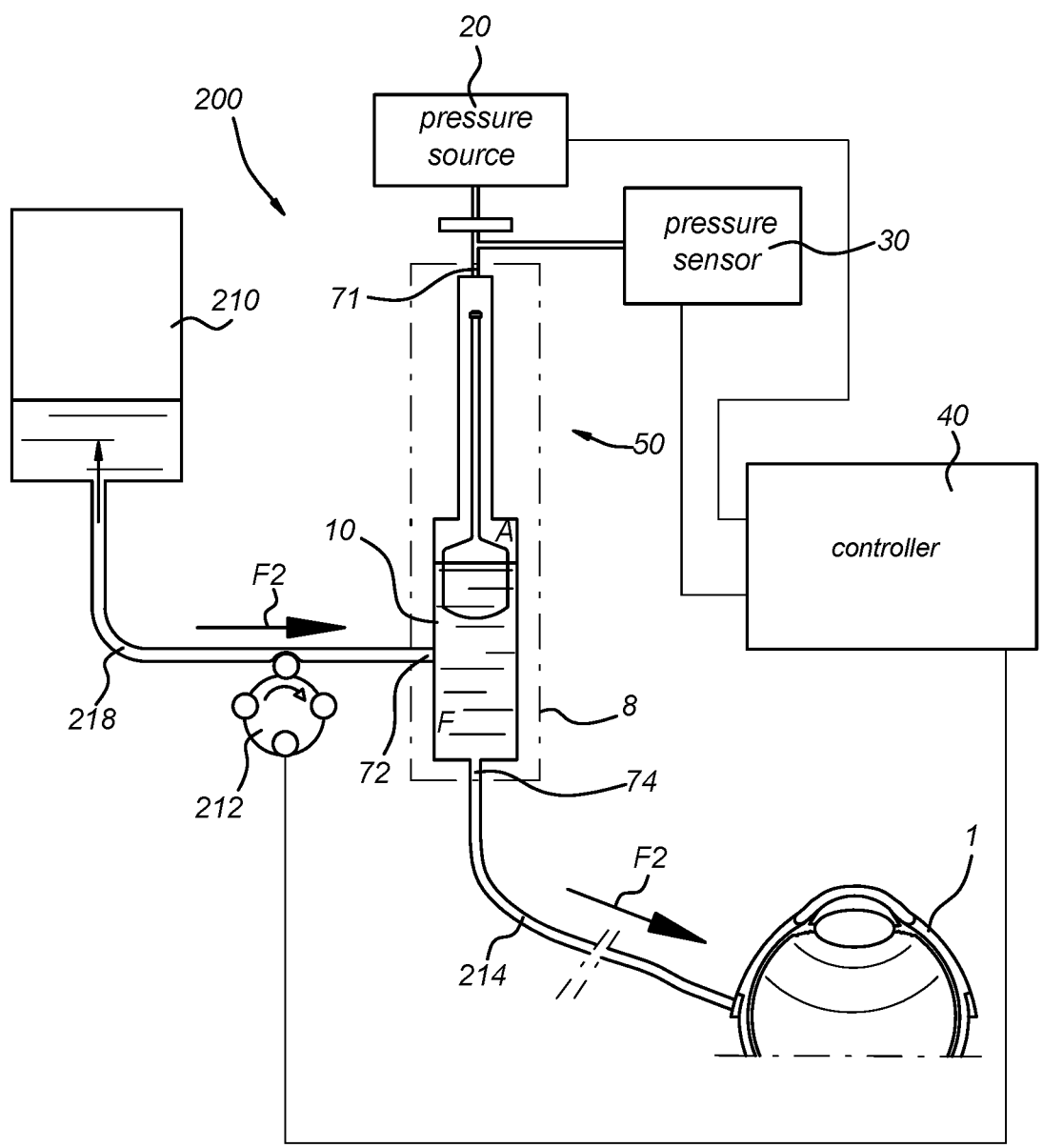
FIG. 1 shows an irrigation system for irrigating the eye during an ophthalmic surgical procedure.

An active irrigation system according to the present invention will now be described with reference to FIG. 1. As shown in FIG. 1, an irrigation system 200 comprises a cassette 8, sometimes referred to as a surgical cassette, having a chamber 10. The chamber 10 is configured to store a fluid F in a lower part 10b of the chamber 10 and air A in an upper part 10a of the chamber 10, the upper part 10a being the remaining space at the top of the chamber 10. The chamber 10 comprises at least one fluid port 72; 74 for introducing an irrigation fluid F into the chamber 10 from a fluid source, e.g. an infusion bottle 210 into the chamber 10 and for delivering irrigation fluid F from chamber 10 to an irrigation tip (not shown) via an irrigation line 214. The surgical irrigation tip can be used to deliver irrigation fluid to a surgical site, e.g. the eye 1.

In some embodiments, the fluid inlet port 72 and fluid outlet port 74 are combined as a single fluid port directly connected to the chamber 10. The fluid port 72; 74 then splits into an input connection to a first conduit (such as infusion conduit 218 in the FIG. 1 embodiment), and an output connection to a second conduit (irrigation conduit 214 in the FIG. 2 embodiment). This is possible as the chamber 10 controls the flow of fluid into or out of the fluid port 72; 74 by pressure control. In other embodiments, the chamber 8 is provided with a dedicated fluid inlet port 72 and a dedicated fluid outlet port 74.

In other words, the chamber can be configured in two ways: in some embodiments, the at least one fluid port comprises a single fluid port configured to introduce fluid into the chamber from a fluid source and deliver fluid from the chamber to a surgical site. In alternative embodiments, the at least one fluid port comprises a first fluid port 72 configured to introduce fluid into the chamber 10 and a second fluid port 74 configured to deliver fluid F from the chamber 10 to the surgical site. In any event, the pressure control system controls the flow of fluid into and out of the chamber 8 via the fluid port(s).

An irrigation fluid pump 212 (e.g. a peristaltic pump) is configured to move fluid F from the (infusion) fluid source 210 to the chamber 10. The irrigation pump 212 may be provided between the fluid source 210 and the chamber 10, along infusion line 218. A variable pressure source 20 is provided in fluid communication with the chamber 10 and is configured to pressurise the chamber 10. A pressure sensor 30 is provided in fluid communication with the chamber 10 and is configured to measure the pressure within the chamber 10. The pressure sensor 30 may be arranged to measure either the air pressure or the liquid pressure, and may be selected as any suitable pressure sensor, such as a diaphragm, piezo-resistive or a MEMS based pressure sensor.

A controller 40 is operatively connected to the pressure sensor 30 and the variable pressure source 20 and is configured to adjust the pressure provided by the variable pressure source 20 to maintain the pressure within the chamber 10 at a desired level.

Active control of the irrigation pressure within the surgical irrigation system 200 is achieved in the following manner. Before or during an irrigation procedure, a healthcare practitioner determines a suitable irrigation pressure and provides a pressure set-point(s) to the system 200 using a suitable user interface (not shown). The interface may by a digital interface such as a GUI, or it may be a foot pedal or dial. The user interface is not critical to the present invention.

Under the direction of the controller 40, the irrigation pump 212 moves the fluid F from the (infusion) fluid source 210 through the fluid port 72 to the chamber 10, partially filling the chamber 10 with fluid F. The lower part of the chamber 10 is filled with irrigation fluid F, the remaining space in the upper part of the chamber 10 is filled with air A. The variable pressure source 20 moves the fluid (F) from the chamber 10 to the fluid port 72 (or to a dedicated outlet port 74), and eventually to a surgical site, by applying a positive pressure to pressurize the chamber 10 via the pressure port 71. The flow of fluid through the system 200 is indicated by arrow F2.

The pressure sensor 30 measures the pressure within the chamber 10 and provides information regarding the actual pressure within the chamber 10 to the controller 40. It will be appreciated that the actual pressure within the chamber 10 varies even when a constant pressure is delivered by the pressure source 20 due to variables that are outside the healthcare practitioner's control (e.g. temporary occlusions in the irrigation and aspiration lines used in a surgical procedure and the resultant sudden drop in pressure that follows the removal of such an occlusion).

To compensate for these variations, the pressure within the chamber 10 is adjusted by adjusting the pressure applied by the variable pressure source 20 in response to feedback from the pressure sensor 30 to maintain a predetermined irrigation pressure within the chamber 10. The set-point for the pressure within the chamber 10 may be a constant irrigation pressure or it may be a varying pressure profile. The variable pressure source 20 selectively applies a positive or negative pressure through the pressure port 71 to correct an over- or under-pressurisation of the chamber 10 compared to the predetermined set-point. For example, if the pressure within the chamber 10 (as measured by the pressure sensor 30) is too high, the pressure source 20 can be configured to apply a reduced (or negative pressure) to bring the pressure within the chamber 10 back within range.

By pressurising the chamber 10, irrigation fluid F can be delivered to the eye 1 at a pressure determined by a medical practitioner, independent of the conditions at the surgical site. This allows the system 200 to compensate for fluctuations in irrigation pressure and/or flow due to temporary occlusion of aspiration or irrigation lines and the subsequent removal of those occlusions. This allows greater stability within the surgical site (e.g. the eye 1). The arrangement shown in FIG. 1 also provides an advantage over systems in which the infusion fluid source is directly pressurised (e.g. where the infusion bottle is squeezed) since the pressure across the various infusion and irrigation lines and an intervening chambers in such systems is difficult to control.

The variable pressure source 20 is at least capable of applying a variable positive pressure to the chamber 10 to deliver fluid from the chamber 10 to the eye 1 via an irrigation line 214. However, the variable pressure source 20 can be configured to selectively apply a positive pressure and a negative pressure to the chamber 10. Such a configuration is advantageously versatile and can be used to quickly correct excessively high and/or low pressures within the chamber 10. A variable pressure source 20 suitable for use in connection with the present invention is described with reference to FIGS. 5A and 5B. However, the skilled person will appreciate that other variable pressure sources may be employed.

The irrigation system 200 shown in FIG. 1 may also comprise a fluid level indicator 50 arranged to measure the fluid level within the chamber 10 during operation. The fluid level indicator 50 can be arranged within the cassette 8 in which the chamber 10 is provided. The fluid level indicator 50 may be configured to measure the fluid level remote from the fluid/air interface W within the chamber 10. In an exemplary embodiment, the fluid level indicator 50 may be a float based fluid level indicator, as described in more detail with refer to FIG. 4. However, the skilled person will appreciate that other fluid level indicating arrangements are possible.

The controller 40 will now be described in more detail with reference to FIG. 2, which shows a schematic of a controller 40 suitable for use in the irrigation system 200 of FIG. 1. The controller 40 comprises a pressure controller 42 for maintaining a desired pressure within the chamber 10 and a fluid level controller 43 for controlling the fluid level within the chamber 10, e.g. by maintaining the fluid level within a pre-determined range.

The pressure controller 42 receives pressure information from the pressure sensor 30 and adjusts the pressure delivered by the variable pressure source 20 to maintain the pressure within the chamber 10 at the desired level, as described above with reference to FIG. 1. The pressure controller 42 can be programmed to provide a varying pressure profile or to maintain the pressure within the chamber 10 within a predefined range. As an example, if the pressure within the chamber 10 drops below a predetermined threshold (e.g. as a result of a spike in aspiration flow away from the surgical site), the pressure controller 42 adjusts the set-point for the variable pressure source 20 to increase the pressure within the chamber 10, thereby increasing the flow of irrigation fluid to compensate for the sudden drop in pressure. Conversely, if the pressure controller 42 determines via the pressure sensor 30 that the pressure within the chamber 10 is too high (e.g. as a result of occlusion of the aspiration line), the pressure controller 42 instructs the variable pressure source 20 to supply a decreased pressure (or a negative pressure) to correct the over-pressurisation of the chamber 10.

Figure 2:
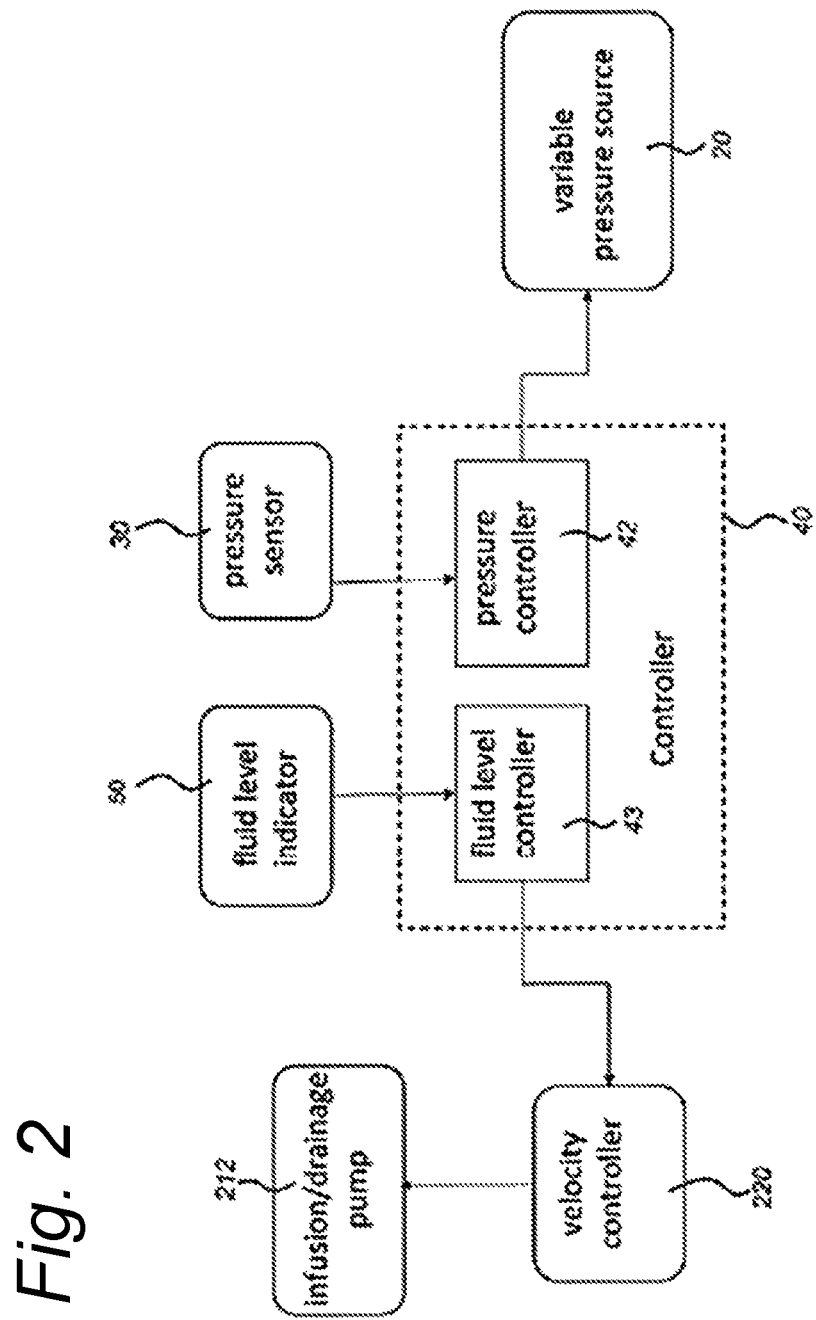
FIG. 2 shows a schematic of the controller employed in the system of FIG. 1.

The controller 40 also comprises a fluid level controller 43 for controlling the fluid level within the chamber 10, as shown schematically in FIG. 2. The fluid level controller 43 is configured to maintain the fluid level W within the chamber 10 within a predefined range by adjusting the rate at which the irrigation pump 212 moves fluid from the fluid source 210 to the chamber 10 based on feedback from the fluid level indicator 50. The fluid level controller 43 provides a set-point to a velocity controller 220, which controls the rate at which irrigation pump 212 delivers irrigation fluid F to the chamber 10 from the infusion bottle 210. As an example, if, based on feedback from the fluid level indicator 50, the controller 40 determines that the fluid level within the chamber 10 is too low, the controller 40 adjusts the set-point of the velocity controller 220 to increase the rate/speed at which irrigation pump 212 delivers irrigation fluid from the infusion bottle 210 to the chamber 10. Conversely, if the controller 40 determines that the fluid level within the chamber 10 is too high, the controller adjusts the set-point of the velocity controller 220 to decrease the rate/speed at which the irrigation pump 212 delivers fluid from the infusion bottle 210 to the chamber 10.

Advantageously, the controller 40 shown in FIG. 2 can also allow for calculation of the flow rate to the eye 1 without the need for a flow sensor within the irrigation line 214. The controller is configured to calculate the irrigation flow through the irrigation tip based on the fluid level measured by the fluid level indicator 50 and/or the infusion rate determined by the velocity controller 220. Since the dimensions of the fluid port (s) 72; 74, the irrigation line 214 and the irrigation tip (not shown) are known, and the pressure within the chamber 10 is sensed by the pressure sensor 30, the irrigation pressure and the irrigation flow rate at the irrigation tip can be calculated without direct measurement at the surgical site. This is advantageous because ophthalmic surgical systems often have small flow rates (as they comprise narrow gauge irrigation lines), for which accurate flow sensing can be challenging. It is noted that even without fluid level information, it is possible to only use the infusion rate determined by the velocity controller 220 (i.e. the actual velocity of a (peristaltic) pump 212.

The above description of FIG. 2 relates to a pressure mode of operation, wherein a user can input a set point for the desired pressure to pressure controller 42. This may be applied both when the present invention embodiments are used for controlling irrigation to the eye, and for controlling aspiration from the eye. In a further embodiment, specifically suited for aspiration purposes, the present invention embodiments are operated in a flow control mode. In the flow control mode, a set point for the desired aspiration flow is input to the velocity controller 220, for controlling the speed of the drainage pump 212. The fluid level controller 43 uses the input from the fluid level indicator 50 to provide a pressure set point to the pressure controller 42 that subsequently control the variable pressure source 20 to ensure the fluid level is controlled to an internal defined set point.

The controller 40 of FIG. 2 may also be employed to alert the user to an empty bottle condition (e.g. when the infusion bottle is empty/low of fluid). This minimizes the risk of air entering the irrigation line 214, which can be dangerous.

An empty bottle warning system may issue a warning signal or alarm when a predetermined volume of irrigation fluid has been delivered by the velocity controller 220. The extracted volume can be calculated based on the initial quantity of irrigation fluid in the infusion bottle 210 and the amount of the fluid delivered to the chamber 10 by the velocity controller 220. A warning can be issued when the volume of fluid delivered approaches the total initial volume of the infusion bottle 210.

However, the active irrigation system 200 described above also allows for an empty bottle warning system that does not require precise knowledge of the initial fluid volume contained within the infusion bottle 210. Instead, the controller 40 can be configured to monitor the level of fluid within the chamber 10 during operation and issue a warning signal if the fluid level moves out of predefined range, e.g. falls below predefined threshold.

As described above, the fluid level controller 43 monitors the fluid level within chamber 10 and adjusts the set-point of the velocity controller 220 to maintain the fluid level with the chamber 10 within the desired range. In an empty bottle condition, air will be transported into the chamber 10. This will cause the fluid level within the chamber 10 to fall, even if the velocity controller 220 increases the rate at which pump 212 delivers fluid to the chamber 10. This in turn causes the fluid level in the chamber 10 to drop out of range, which can trigger a warning signal or alarm to be issued, prompting the user to replace the infusion bottle 210. This system is advantageous because it does not require prior knowledge of the volume of irrigation fluid in bottle 210 or the rate of flow of fluid into the chamber 10. Moreover, by monitoring the level of fluid in the chamber 10, a warning signal can be produced before the chamber 10 is empty, thereby minimizing the risk that air is delivered through the irrigation line 214 to the eye.

Figure 3:
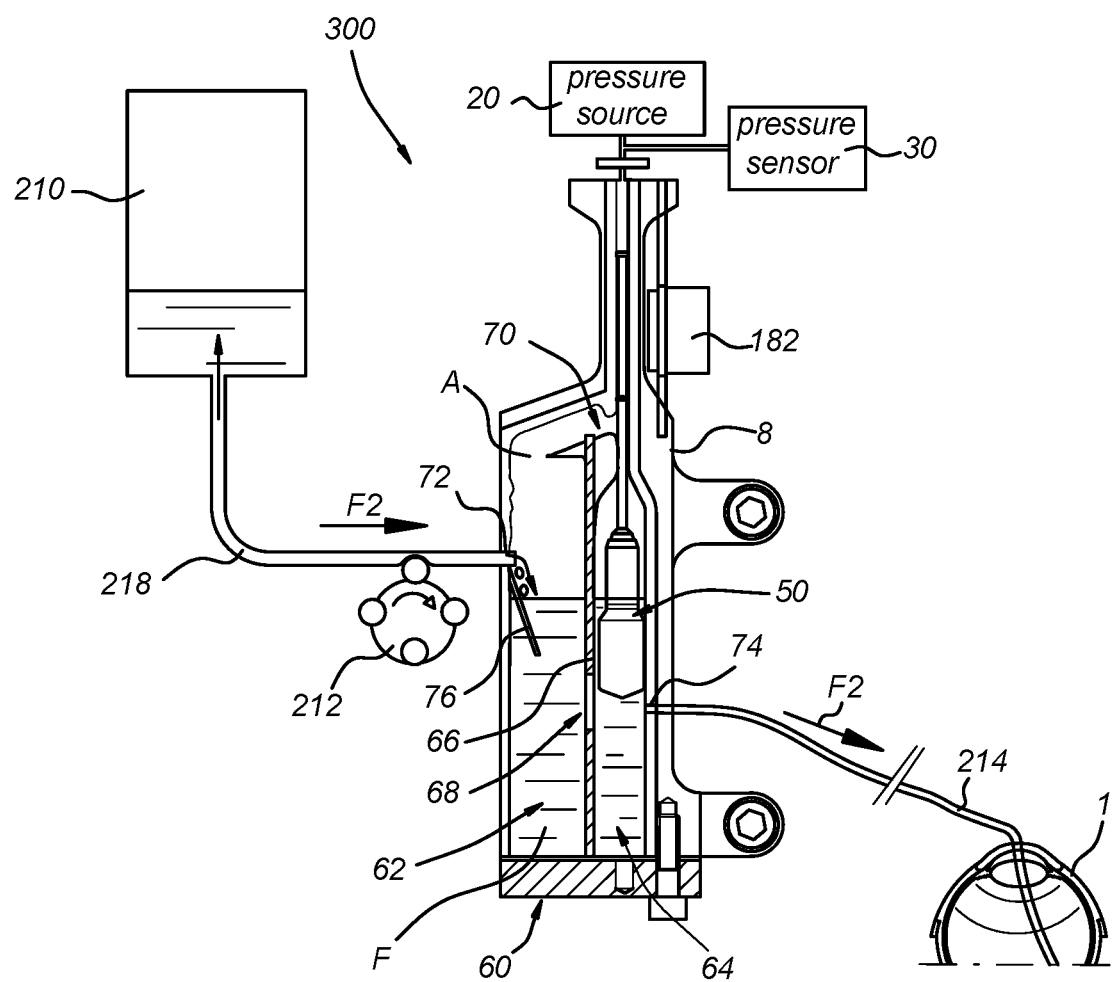
FIG. 3 shows an irrigation system according to another embodiment of the present invention.

Referring now to FIG. 3, in at least one embodiment, the irrigation system 200 described with reference to FIG. 1 can be modified to include a chamber 60 configured for air removal (e.g. minimizing the risk that air bubbles from the infusion line 218 can enter the irrigation line 214).

As shown in FIG. 3, the irrigation system 300 is generally similar to the irrigation system 200 described with reference to FIG. 1 and comprises an infusion bottle 210 and an irrigation pump 212 to deliver fluid from the infusion bottle 210 to a chamber 60 comprised in a surgical cassette 8 via an irrigation line 214. A velocity controller 220 as shown schematically in FIG. 3 controls the rate of flow of fluid F from the infusion bottle 210 to the chamber 60. A variable pressure source 20 and a pressure sensor 30 are in fluid communication with the chamber 60 via the pressure port 71. A pressure controller 42 monitors the pressure within chamber 60 and controls the variable pressure source 20, as described above, to maintain a desired irrigation pressure within chamber 60. The surgical cassette 8 comprises a fluid level indicator 50 to monitor the fluid level with chamber 60.

Whilst the chamber 10 described above with reference to FIG. 1 comprises a fluid (inlet) port 72 (connected to the infusion line 218) in the lower part of the chamber 10 (i.e. below the fluid surface during normal operation), the chamber 60 shown in FIG. 3 comprises a fluid port comprising a fluid inlet port 72, which is provided in an upper portion of the chamber 60, such that the fluid inlet is provided above the fluid surface W within the chamber 60 during operation. By providing a fluid inlet port 72 above the surface W of the fluid F, air bubbles from the (infusion) fluid source 210 and the infusion line 218 are not introduced below the fluid surface W. This minimizes the risk of bubbles being introduced into the irrigation line 214 and bubbles forming beneath the surface on the float-based fluid level indicator 50, which could adversely affect fluid level measurement. As the fluid level may actually change during use, the fluid inlet port 72 is positioned in the top half of the chamber 60, e.g. in the top third of the chamber 60. On the other hand, the fluid inlet 72 is also positioned or arranged to allow non-turbulent input of the fluid into chamber 60, to prevent e.g. bubbles being formed in the fluid.

In any event, the fluid inlet port 72 is configured such that when the fluid level is within the desired range, the fluid inlet port 72 is above the fluid surface (i.e. the air/liquid interface), when the fluid level is within the normal operating range. This configuration ensures that any air bubbles introduced into the infusion line 218 are not introduced below the surface W of the fluid F within the chamber 60, which could lead to bubbles being introduced into the irrigation line 214 or disturbances at the fluid/air interface W that could adversely affect fluid level measurement.

To prevent falling droplets impacting the fluid level indictor 50, the chamber 60 comprises a first compartment 62 and a second compartment 64 separated by an internal wall 66. The first compartment 62 comprises the fluid port 72; 74 and the second compartment 64 comprises the fluid level indicator 50. The internal wall 66 comprises at least one opening 68 therein to allow the fluid level in the first compartment 62 and the second compartment 64 to equalize. By providing separate compartments for the fluid port 72; 74 and the fluid level indictor 50, surface ripples formed by fluid droplets hitting the fluid surface W within the first compartment 62 from cannot propagate into the second compartment 64 due to internal wall 66. This ensures minimum disturbance in the fluid surface in the second compartment 64, where fluid level measurements are made. This may allow for more accurate fluid level measurement.

Furthermore, the internal wall 66 will also prevent any splashing of fluid originating from the fluid inlet 72 onto the outer surface of the float which is part of the fluid level indicator 50 as drawn in the embodiment of FIG. 3. This will prevent a possibility of the float sticking at the inside of the second compartment 64, which might also influence proper operation of the fluid level indicator 50.

In any event, the first opening 68 should be positioned such that it is below the fluid surface when the fluid level is within the normal operating range. The specific location of the first opening 68 can be determined by the skilled person based on the operating parameters of the system. E.g. the first opening 68 is positioned below the fluid port 72, which would prevent any possible bubbles being formed to reach the float of the fluid level indicator 50. In an even further embodiment, the first opening 68 may be even at the bottom side of the chamber 60, and would then (as in the other positions described above) also act as a dampening element for the fluid level in the second compartment 64.

In some embodiments, the internal wall 66 comprises a second opening 70 in the upper part of the chamber 60 to allow the air pressure in the first compartment 62 and the second compartment 64 to equalize. The second opening 70 can be formed as a bore through an internal wall 66 that extends all the way to the top of the chamber 60. Alternatively, the internal wall may stop short of the upper wall of the chamber 60, thereby providing an opening 70 at the upper end of the chamber 60.

In any event, the second opening 70 should be positioned such that it is above the fluid surface when the fluid level is in range. The specific location of the first opening 68 can be determined by the skilled person based on the operating parameters of the system. The specific location of the second opening 70 can also be determined by the skilled person based on the operating parameters of the system.

As shown in FIG. 3, in some embodiments a dedicated fluid outlet port 74 can be provided in the second compartment 64. This further reduces the risk of disturbances/bubbles produced by fluid droplets entering the chamber 60 from entering the irrigation line 214. However, the skilled person will recognize that the fluid outlet port 74 may be provided in the first compartment 62 (or possibly combined in a single port with the fluid inlet, as described above), leaving the fluid level sensor 50 with a dedicated compartment 64. As the fluid in the chamber 60 with the application to irrigation only will originate only from the fluid source, there will be virtually no debris present in the fluid in chamber 60 during use, and hence the fluid outlet port 74 may be positioned in the bottom part of chamber 60, possibly even at the bottom.

Furthermore, by selecting a position of the fluid outlet port 74 and/or first opening 68 away from the float of the fluid level indicator 50, any possible sideways flow of the fluid in the vicinity of the float is prevented, which will improve the accuracy and proper operation of the fluid level indicator 50.

The fluid level indicator 50 shown in FIG. 3 (and described in more detail with respect to FIG. 4) is a float based fluid level sensor. However, the skilled person will appreciate that the advantages of a divided chamber may also be realized in systems with alternative fluid level sensing means. For example, minimizing disturbances in the fluid surface may also be advantageous in direct fluid level measurement systems, e.g. systems in which optical or electrical sensors detect the position of the air/fluid interface.

Optionally, to further minimize pressure disturbances in the chamber 60 caused by falling droplets, the fluid inlet port 72 may open onto a inclined surface 76 down which droplets from the fluid inlet port 72 can glide into the fluid F. This will also further minimize the chance of bubbles being formed in the fluid F by falling droplets from the fluid inlet port 72.

Although the exemplary irrigation system described with reference to FIG. 3 is advantageous, the skilled person will appreciate that the split level chamber 60 described above with reference to FIG. 3 may also be employed in an irrigation system in which the fluid inlet port 72 is provided toward the bottom of the chamber 60, i.e. below the fluid surface. The internal wall 66 may limit the passage of air bubbles introduced at the fluid inlet port 72 in the first compartment 62 to into the second compartment 64, thereby minimizing the risk of bubble formation around the fluid level indicator 50 (which could cause the float to stick to the sides of the chamber 60). The two-chamber arrangement may also limit bubble formation at the fluid surface, which can adversely affect the accuracy of fluid level measurement.

Figure 4:
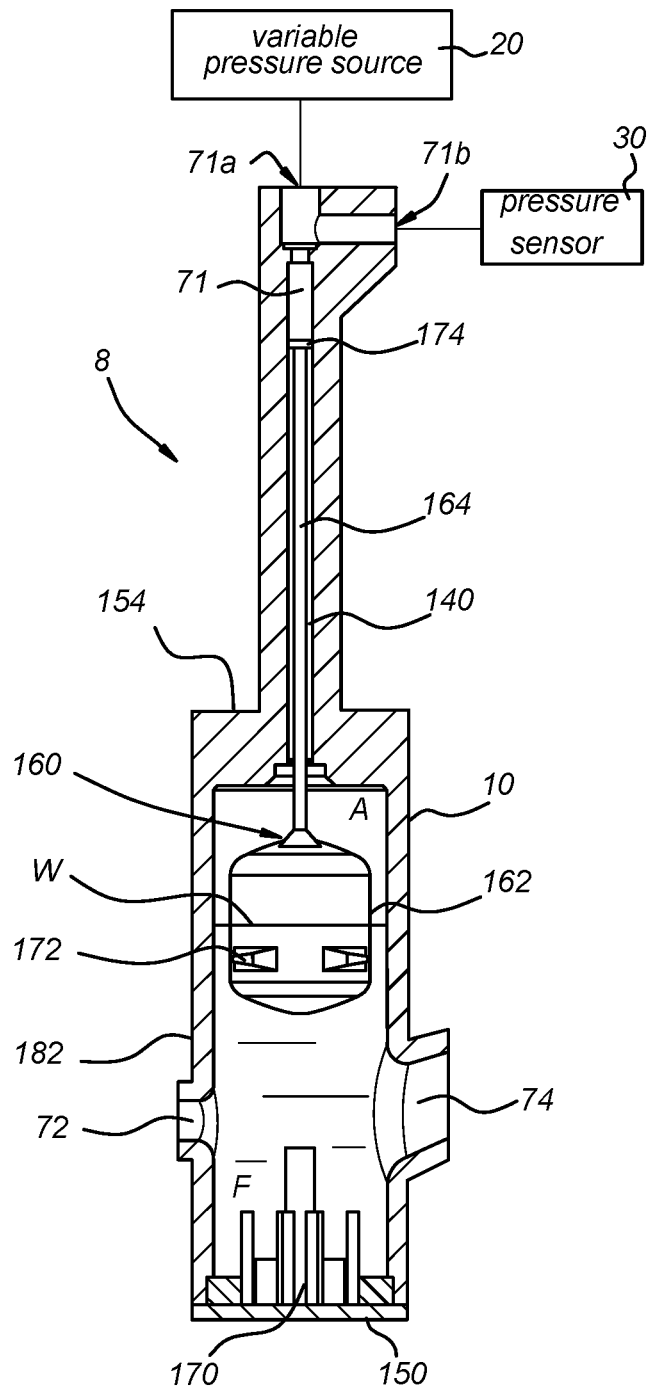
FIG. 4 shows a float based fluid level indicator for indicating the level of fluid within a chamber of an irrigation system in accordance with the present invention.

In some exemplary embodiments of the irrigation system 200, 300, the fluid level indicator 50 is a float-based fluid level indicator. Referring now to FIG. 4, the float-based fluid level indicator 50 comprises at least one float 160 configured to rise and fall with the fluid level W within the chamber 10. As shown in FIG. 4, the cassette 8 comprises a chamber 10 having a channel 140 extending therefrom.

The float 160 comprises a float body 162, which is disposed within the chamber 10, and a float stem 164, which is disposed at least partially within the channel 140. The float body 162 and the float stem 164 are arranged such that they are free to move within the chamber 10 and channel 140 respectively, as the fluid level W rises and falls. The cassette 8 is configured so that the position of the float stem 164 within the channel 140 can be measured by a sensing system that detects the position of the float stem 164 within the channel 140. The fluid level W within the chamber can thus be determined by measuring the position of the float stem 164 within the channel 140. The position of the float stem 164 within the channel 140 can be sensed with means known to the person skilled in the art, e.g. optically, acoustically, electronically, etc.

By measuring the position of the float stem 164 within the channel 140, the level of the fluid F within the chamber 10 can be made indirectly, i.e. remote from the air/liquid interface W within chamber 10. This is advantageous because such a measurement is generally insensitive to changes in liquid properties within the chamber which may affect the liquid surface, e.g. disturbances in the fluid surface due to fluid ingress from the infusion bottle 210. It also allows fast and reliable fluid level sensing, which allows fine control of the fluid level within the chamber 10 by the controller 40, as described above with reference to FIG. 3.

The float based fluid level sensor 50 is described above with reference to a chamber 10 having a single compartment. However, the skilled person will appreciate the float-based fluid level indicator described with reference to FIG. 4 can also be employed in a multi-compartment chamber, such as chamber 60.

A variable pressure source 20 suitable for use in the active irrigation system according to the present invention will now be described with reference to FIGS. 5A and 5B.

Figure 5A:
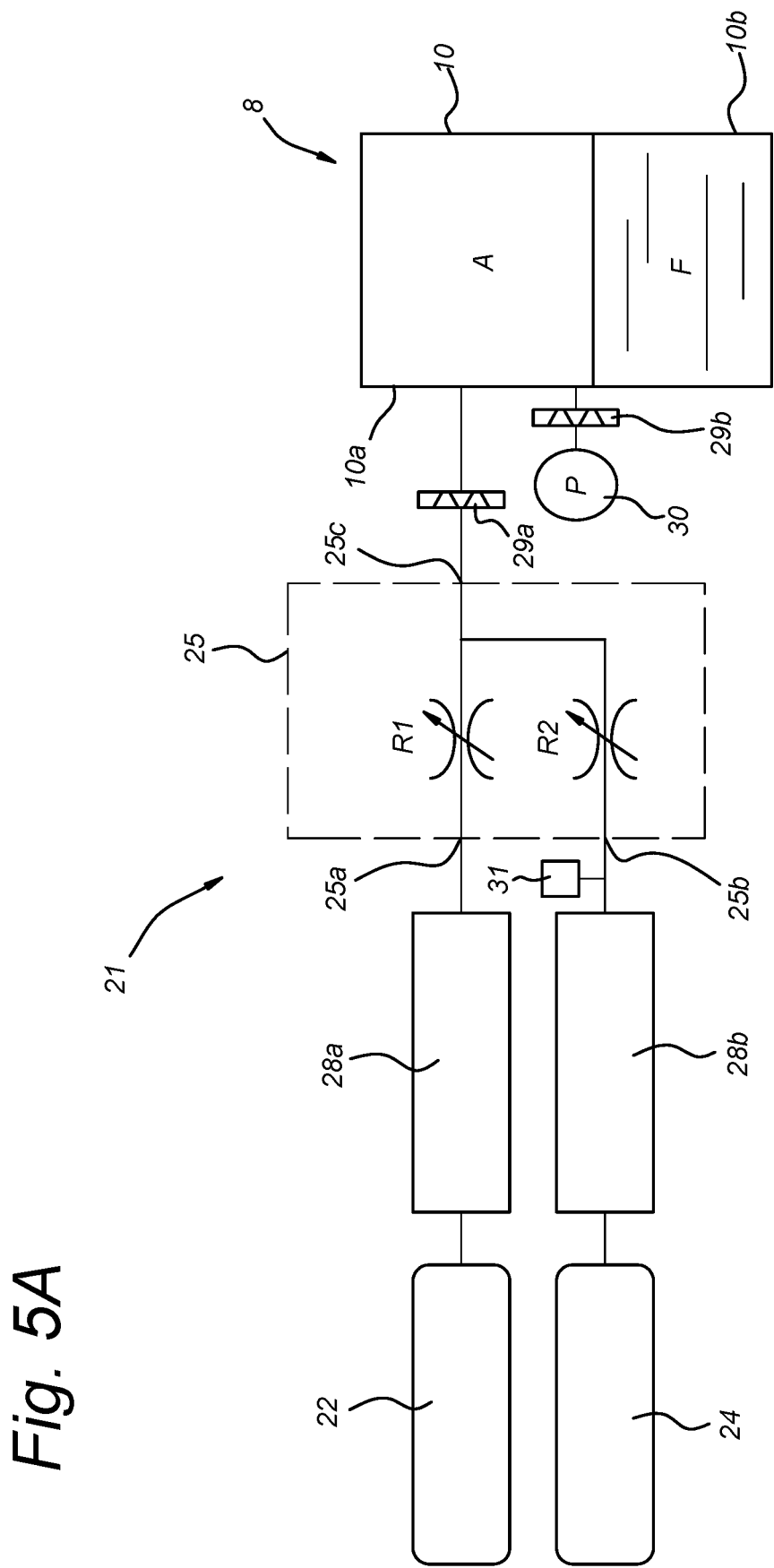
FIGS. 5A and 5B show a variable pressure source for use with an irrigation system in accordance with the present invention.
Figure 5B:
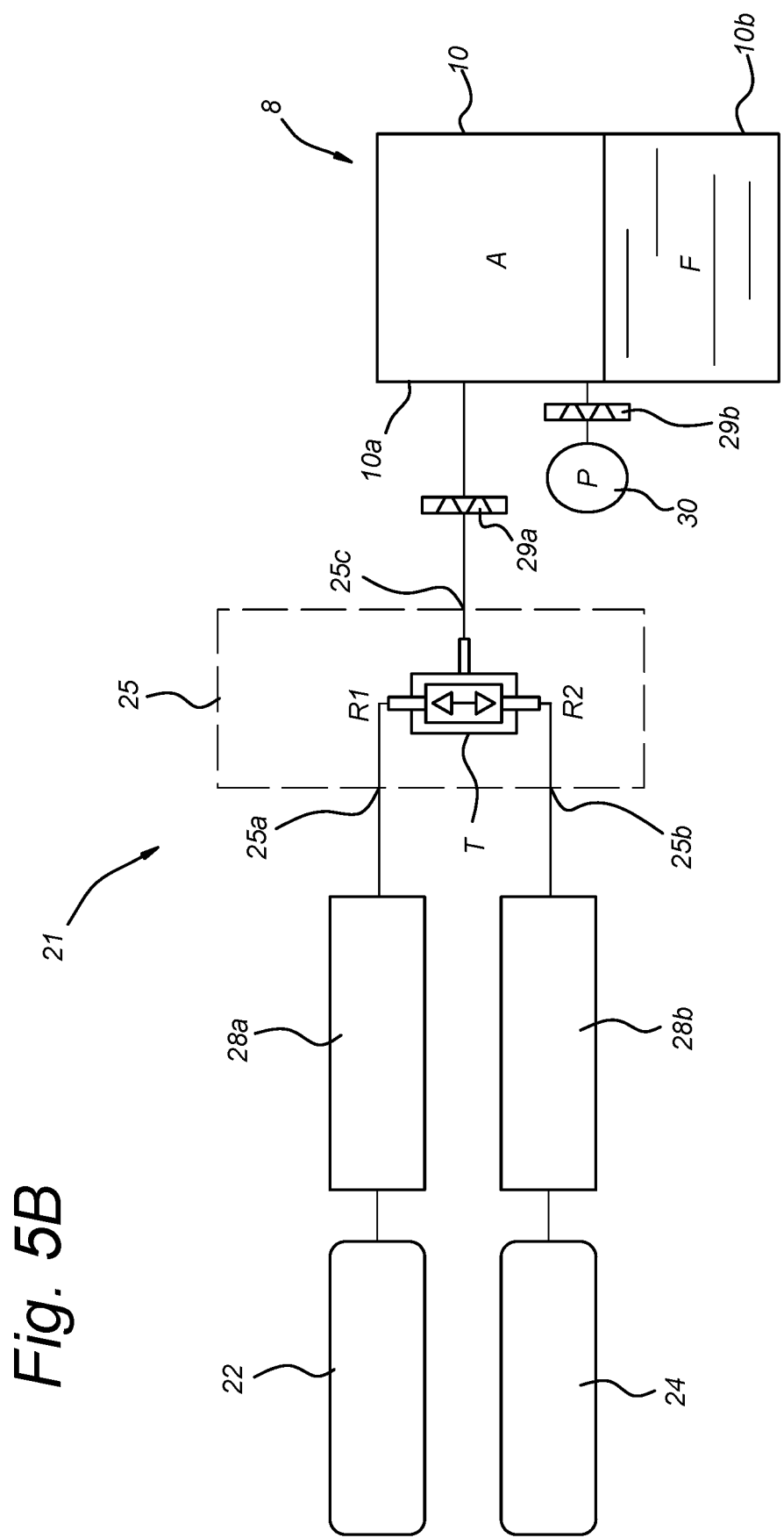

FIGS. 5A and 5B each depict an embodiment of a variable pressure source 20 that comprises a pump unit 21 having a negative pressure source 22 (e.g. a vacuum source) and a positive pressure source 24 (e.g. a compressor). In an embodiment, the negative or positive pressure source 22, 24 may be a membrane pump for example, although the skilled person will appreciate that other positive and/or negative pressure sources could be employed. The terms negative and positive pressure are being used herein with respect to an ambient pressure. As an alternative implementation one of the pressure sources 22, 24 could be actually at the ambient pressure.

The pump unit 21 is further provided with an adjustable valve arrangement 25, wherein the valve arrangement 25 comprises a vacuum port 25a connected to the negative pressure source 25 and a pressure port 25b connected to the positive pressure source (24). The adjustable valve arrangement 25 also comprises a main port 25c in fluid communication with the vacuum port 25a and/or the pressure port 25b. The main port 25c is configured to connect to an upper part 10a of a chamber 10 for storing air A and exchanging the air A with the pump unit 21. The chamber 10 comprises a bottom part 10b for storing a surgical fluid F to be irrigated or aspirated.

The adjustable valve arrangement 25 is adapted to control the flow of air to/from the chamber 10 through the main port 25c corresponding to the intensity at which the vacuum source 22 and/or the pressure source 24 is/are active. Since the valve arrangement 25 shown in FIGS. 5A and 5B couples the chamber 10 to a negative pressure source 22 as well as a positive pressure source 24, the pump unit 21 is able to provide fast, dynamic pressure control within chamber 10 and with remarkable precision rather than solely relying on a vacuum source to vary the pressure within the chamber 10. The valve arrangement 25 of the present invention is thus configured to provide virtually any pressure required at the main port 25c below or above atmospheric pressure with any desired speed and accuracy.

In an embodiment, the adjustable valve arrangement 25 is a proportionally adjustable valve arrangement allowing smooth and continuous changes in air pressure and air flow across the main port 25c. The proportionally adjustable valve arrange is capable of switching between and/or "blending" the negative and positive pressure sources 22, 24, so that any desired pressure and air flow across the main port 25c can be achieved with great speed and precision. As an alternative implementation, a pulse width modulation (PWM) controlled on/off valve arrangement may be applied In an exemplary embodiment as shown in FIG. 5A, the adjustable valve arrangement 25 comprises a first adjustable valve R1 connected between the vacuum port 25a and the main port 25c and a second adjustable valve R2 is connected between the pressure port 25b and the main port 15c. This allows virtually any amount of negative pressure from the negative pressure source 22 and any amount of positive pressure from the positive pressure source 24 to be accurately controlled at the main port 25c, so that any desired net pressure and air flow across the main port 25c can be achieved with great accuracy and speed (within the negative and positive pressure ranges of the vacuum source 22 and/or pressure source 24).

In an advantageous embodiment, the first adjustable valve R1 is a first proportional valve and the second adjustable valve R2 is a second proportional valve. Each of the proportional valves R1, R2 allow for fast, continuous control to further increase speed and accuracy of the net pressure and air flow across the main port 25c.

Controlling the first and second adjustable/proportional valves R1, R2 with e.g. a current source can be advantageous because current controlled valves may be less insensitive for temperature variations, when compared to voltage controlled valves. Alternatively, the first and second adjustable/proportional valves R1, R2 are position controlled valves.

In a further embodiment, the first and second adjustable/proportional valves R1, R2 are biased with a first current to allow a bias flow in the flow path between negative pressure source 22 and positive vacuum source 24, whilst maintaining a net zero flow through the main port 25c (keeping pressure in the chamber 10 at a constant level). In general, the current/flow characteristic of such a valve includes a threshold current below which the valve remains closed. Biasing the first and second adjustable/proportional valves R1, R2 with a current at least equal to this threshold current allows to have a faster response time when further opening one of the valves R1, R2 during control.

To allow control and proper setting of the adjustable valve arrangement 25, the pressure control unit may further comprise a flow sensor 31 arranged in a bias flow path between the negative pressure source 22 and the positive pressure source 24. The bias flow path comprises the direct connection parts between the negative pressure source 22 and the positive pressure source 24 in any of the exemplary embodiments described herein. E.g. the flow sensor 31 is arranged between the positive pressure source 24 and the pressure port 25b or between the vacuum source 22 and the vacuum port 25a. The flow sensor 31 can be any suitable flow sensor, e.g. an in-line flow sensor.

The flow sensor 31 may be connected to the controller 40 (or to a dedicated controller), and may be implemented as a mass flow sensor or as a volumetric flow sensor (e.g. a differential pressure based flow sensor which allows measuring a volumetric flow rate by measuring a differential pressure over a (fixed) restriction). The measurement data from the flow sensor 30 can then be used in a secondary control loop which actively controls the flow in the bias flow path (without affecting flow through the main port 25c).

Referring to FIG. 5B, in an alternative embodiment, the adjustable valve arrangement 25 is a three-way valve arrangement T, which may be seen as a single, unitary valve manifold having three connecting ports 25a, 25b, 25c and a valve insert for controlling/dividing air flow through these connecting ports. For example, the three-way valve arrangement 25 comprises the vacuum port 25a, the pressure port 25b, and the main port 25c, wherein the valve insert allows accurate control of the degree in which the vacuum port 25a or the pressure port 25b is in communication with the main port 25c.

As with the first and second adjustable/proportional valves R1, R2, the three-way valve arrangement T may be current controlled, thereby reducing or avoiding temperature dependent valve sensitivities. Note that the skilled person will of course appreciate that voltage control may still be effectively used to control the adjustable valve arrangement 25, in particular the first and second adjustable/proportional valves R1, R2 as well as a three-way valve arrangement T as described above.

In order to monitor the pressure within the chamber 10 during operation, an embodiment is provided wherein the pump unit 21 comprises a pressure sensor 30 in communication with the main port 25c. For example, in an embodiment the pressure sensor 30 is connected to a conduit arranged between the main ports 25c and the upper part 10a of chamber 10. Note that in an embodiment a controller can be provided and configured to adjust the adjustable valve arrangement 25 to maintain a desired pressure in the chamber 10 in response to the pressure measured by the pressure sensor 30.

During a surgical procedure, also discussed above with reference to FIG. 3 as pressure sensor 30, the pressure sensor P as depicted in FIG. 5A can provide feedback to a controller 40 for adjusting the valve arrangement 25 to maintain the pressure within chamber 10 at a desired level. For example, if the sensed pressure within the chamber 10 is lower than the desired pressure, the pressure can be quickly increased by adjusting the valve arrangement 25 to deliver pressurised air from the positive pressure source 24 to the main port 25c and thus to the chamber 10. Should the sensed pressure within the chamber 10 be higher than the desired pressure, the pressure can be quickly decreased by adjusting the valve arrangement 25 such that a negative pressure is applied to the main port 25c and thus to the chamber 10. This allows for rapid adjustment of the pressure within the chamber 10 e.g. to compensate for non-linearities and valve hysteresis as well as blockages and leaks within the system or at the surgical site.

In an embodiment, the controller 40 controls the first and second adjustable/proportional valves R1, R2 such that if the desired pressure set-point is achieved, the steady state air consumption is minimized to meet the flow capacity of the compressor and the vacuum source.

According to the present invention the adjustable valve arrangement 25 allows for rapid and accurate control of negative and positive air pressure within the chamber 10. To allow this fast pressure changes, short term mass flow rates are required. To be capable of providing these flow rates that might not match the flow capacity of the internal system pressure sources 22, 24, a vacuum buffer 28a and a pressure buffer 28b are used. Furthermore, fast changes in air pressure can induce short bursts of relatively high mass flow rates and pressure ripples through the pump unit 21. To provide dampening of such high mass flow rates and pressure ripples there is provided an embodiment wherein the pump unit 21 further comprises a vacuum buffer 28a arranged between the negative pressures source 22 (i.e. vacuum source) and the vacuum port 25a. In another embodiment a pressure buffer 28b may be provided and arranged between the positive pressure source 24 and the pressure port 25b. Of course, in an advantageous embodiment the pump unit 21 comprises both the vacuum buffer 28a and the pressure buffer 28b, so that short bursts of high mass flow rates to and from the chamber 10 are dampened. The vacuum buffer 28a and the pressure buffer 28b each provide capacitance to momentary absorb some of the high mass flow rate from/to the chamber 10 and in doing so also provide dampening of pressure ripples through the pump unit 21 and in the chamber 10. It is noted that either the vacuum buffer 28a and/or the pressure buffer 28b may alternatively or additionally be formed by using the air volume within the pneumatic tubing between the negative/positive pressure sources 22, 24 and the main port 25c.

As mentioned above, the adjustable valve arrangement 25 allows for rapid changes in air pressure within the chamber 10 for optimizing irrigation and/or aspiration during an ophthalmic procedure. For safety purposes when high pressure pulses occur during operation of the pump unit 21 (e.g. in case of failure of the control unit 21 or one or more of the pneumatic components), the adjustable valve arrangement 25 may further comprise on or more safety valves.

The variable pressure source 20 is described above with reference to a chamber 10 having a single compartment. However, the skilled person will appreciate the variable pressure source 20 described with reference to FIGS. 5A and 5B can also be employed in a multi-compartment chamber, such as chamber 60.

In some embodiments, the chamber 10, 60 has a small air volume (i.e. less than 10 cc). However, the skilled person understands that the chamber 10, 60 may have any air volume for which the control is needed. Note that the air volume is the volume of air within the chamber during normal operation, i.e. when the chamber 10, 60 is filled with fluid within the target range. The target volume of fluid may be between 10-15 cc, which would still allow a fast priming (i.e. filling the cassette 8 and all connecting lines with fluid). The variation in amount of fluid in the chamber 10 during operation is e.g. about 3 cc, which would also still enable proper and accurate level sensing using the fluid level indicator 50. In an exemplary embodiment, the total internal volume of the chamber 10 is about 25-30 cc.

The invention claimed is:

1. An active irrigation system for controlling delivery of irrigation fluid to an ophthalmic surgical site, the irrigation system comprising:

a chamber having a first fluid port for introducing an irrigation fluid from a fluid source into the chamber and a second fluid port for delivering the irrigation fluid to a surgical site;

an irrigation pump configured to deliver irrigation fluid from the fluid source to the chamber;

a variable pressure source in fluid communication with the chamber and configured to pressurize the chamber;

a pressure sensor in fluid communication with the chamber configured to monitor the pressure within the chamber;

a first controller configured to adjust the pressure applied by the variable pressure source to maintain a desired irrigation pressure within the chamber, wherein the first controller is operatively connected to the pressure sensor, the chamber comprising a first compartment and a second compartment separated by an internal wall, the first compartment comprising the first fluid port and the second fluid port, the second compartment comprising a fluid level indicator, and wherein the internal wall comprises at least one opening therein to allow the fluid level in the first compartment and the second compartment to equalize.

2. The active irrigation system according to claim 1, wherein the pressure source is configured to selectively apply a positive pressure and a negative pressure to the chamber.

3. The active irrigation system according to claim 1, further comprising a fluid level indicator arranged to indicate a fluid level within the chamber during operation.

4. The active irrigation system according to claim 3, wherein the fluid level indicator is arranged to measure the fluid level remote from a fluid/air interface within the chamber during operation.

5. The active irrigation system according to claim 3, wherein the irrigation system further comprises a second velocity controller, which controls the rate at which the irrigation pump delivers fluid from the fluid source to the chamber, and wherein the first controller is configured to adjust a set-point of the second velocity controller to maintain the fluid level within the chamber based on feedback from the fluid level indicator.

6. The active irrigation system according to claim 5, wherein the first controller is configured to calculate an irrigation flow to the surgical site based on the fluid level sensed by the fluid level sensor and/or an infusion rate determined by the second velocity controller.

7. The active irrigation system according to claim 1, wherein the first controller is configured to monitor the fluid level in the chamber during operation and issue a warning signal if the fluid level moves out of a predefined range.

8. The active irrigation system according to claim 1, wherein the first fluid port is provided in an upper portion of the chamber.

9. The active irrigation system according to claim 1, wherein the internal wall comprises a second opening in an upper part of the chamber to allow the air pressure in the first compartment and the second compartment to equalize.

10. The active irrigation system according to claim 4, wherein the fluid level indicator is a float-based fluid level sensor.

* * * * *